United States Patent [19]

Walker

[11] 4,163,660
[45] Aug. 7, 1979

[54] BIS-SUBSTITUTED SUCCINAMIDES AND THEIR UTILITY AS HERBICIDES

[75] Inventor: Francis H. Walker, Mill Valley, Calif.

[73] Assignee: Stauffer Chemical Company, Westport, Conn.

[21] Appl. No.: 821,887

[22] Filed: Aug. 4, 1977

Related U.S. Application Data

[60] Division of Ser. No. 546,234, Feb. 3, 1975, Pat. No. 4,056,524, which is a continuation-in-part of Ser. No. 459,438, Apr. 9, 1974, abandoned, which is a continuation-in-part of Ser. No. 410,641, Nov. 12, 1973, abandoned.

[51] Int. Cl.$^2$ .......................... A01N 9/00; A01N 9/22
[52] U.S. Cl. .......................... 71/88; 71/94; 71/95
[58] Field of Search .......................... 71/94, 95, 103, 88

[56] References Cited

U.S. PATENT DOCUMENTS

| | | | |
|---|---|---|---|
| 2,927,126 | 3/1960 | Pursglove | 71/103 |
| 3,334,991 | 8/1967 | Hageman et al. | 71/94 |
| 3,423,470 | 1/1969 | Rohr et al. | 71/103 |
| 3,439,018 | 4/1969 | Brookes et al. | 71/103 |
| 3,453,099 | 7/1969 | Popoff et al. | 71/103 |
| 3,752,661 | 8/1973 | Orlett | 71/103 |
| 3,759,689 | 9/1973 | Hageman et al. | 71/76 |
| 3,769,285 | 10/1973 | Levine | 71/94 |

Primary Examiner—Glennon H. Hollrah
Attorney, Agent, or Firm—Harry A. Pacini

[57] ABSTRACT

Bis-substituted succinamides having the formula

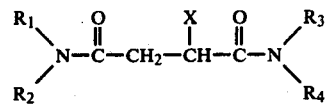

in which X is chlorine or bromine; $R_1$ and $R_3$ are each hydrogen, alkyl, haloalkyl, alkenyl, alkynyl, or benzyl; $R_2$ and $R_4$ are each hydrogen, alkyl, alkenyl, haloalkenyl, alkoxyalkyl, alkynyl, cycloalkyl, cyclopropylmethyl, furfuryl, and tetrahydrofurfuryl; $R_1$ and $R_2$ taken together along with the nitrogen from a non-aromatic heterocyclic ring; $R_3$ and $R_4$ taken together along with the nitrogen form a non-aromatic heterocyclic ring; provided that when $R_1$, $R_2$, $R_3$ and $R_4$ are each alkyl, then one of $R_1$ or $R_2$ and one of $R_3$ or $R_4$ is other than methyl; further provided that only one of $R_1$ or $R_2$ is hydrogen and only one of $R_3$ or $R_4$ is hydrogen. Compounds of this invention are useful as herbicides and includes those compounds in which $R_1$, $R_2$, $R_3$ and $R_4$ are each methyl.

9 Claims, No Drawings

BIS-SUBSTITUTED SUCCINAMIDES AND THEIR UTILITY AS HERBICIDES

This is a division of application Ser. No. 546,234, filed Feb. 3, 1975, now U.S. Pat. No. 4,056,524 which application is a continuation-in-part of U.S. Patent Application Ser. No. 459,438, filed Apr. 9, 1974 now abandoned, which in turn is a continuation-in-part of then copending U.S. Patent Application Ser. No. 410,641, filed Nov. 12, 1973, now abandoned.

This invention relates to certain novel bis-substituted succinamides which can be used as herbicides. More specifically, this invention relates to certain α-halo bis-substituted succinamides, to their preparation and utility of the compounds as herbicides.

The compounds comprising the instant class of compounds correspond to the general formula:

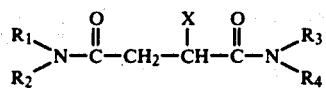

in which x is chlorine or bromine; $R_1$ and $R_3$ are each hydrogen, alkyl having from 1 to 8 carbon atoms, inclusive, haloalkyl having from 1 to 6 carbon atoms, inclusive, in which halo is fluorine, bromine and chlorine, alkenyl having from 2 to 6 carbon atoms, inclusive, alkynyl having from 2 to 8 carbon atoms, inclusive, or benzyl; $R_2$ and $R_4$ are each hydrogen, alkyl having from 1 to 8 carbon atoms, inclusive, alkenyl having from 2 to 6 carbon atoms, inclusive, haloalkenyl having from 2 to 6 carbon atoms, inclusive, in which halo is chlorine or bromine, alkoxyalkyl having from 2 to 8 carbon atoms, inclusive, alkynyl having from 2 to 6 carbon atoms, inclusive, cycloalkyl having from 3 to 7 carbon atoms, inclusive, cyclopropylmethyl, furfuryl, and tetrahydrofurfuryl; $R_1$ and $R_2$ taken together along with the nitrogen form a non-aromatic heterocyclic ring having from 2 to 8 carbon atoms, inclusive; $R_3$ and $R_4$ taken together along with the nitrogen form a non-aromatic heterocyclic ring having from 2 to 8 carbon atoms, inclusive; provided that when $R_1$, $R_2$, $R_3$ and $R_4$ are each alkyl, then one of $R_1$ or $R_2$ and one of $R_3$ or $R_4$ is other than methyl; further provided that only one of $R_1$ or $R_2$ is hydrogen and only one of $R_3$ or $R_4$ is hydrogen.

In the above description, the following preferred embodiments are intended for the various substituent groups: Alkyl and haloalkyl preferably includes, unless otherwise provided for, those members which contain from 1 to 6 carbon atoms, inclusive, in both straight chain and branch chain configurations, for example, methyl, trifluoromethyl, ethyl, 2-chloroethyl, n-propyl, isopropyl, n-butyl, sec.-butyl, 1,1-dimethylbutyl, amyl, isoamyl, n-hexyl, isohexyl, octyl, isooctyl and the like; alkenyl preferably includes, unless otherwise provided for, those members which contain at least one olefinic double bond and containing from 2 to 6 carbon atoms, inclusive, for example, allyl, methallyl, ethallyl, 1-butenyl, 3-butenyl, 2-methyl-1-butenyl, 1-pentenyl, 2-pentenyl, 3-pentenyl, 4-pentenyl, 2-methyl-1-pentenyl, 1-hexenyl, 2-hexenyl, 3-hexenyl, 4-hexenyl, 5-hexenyl and the like; alkenyl and haloalkenyl preferably includes, unless otherwise specified for, those members which contain from 2 to 6 carbon atoms, inclusive, and halo preferably includes chloro or bromo; and alkynyl preferably includes those members which contain from 2 to 8 carbon atoms, inclusive, and at least one acetylenic unsaturation (triple bond), for example, 1-propynyl, 2-propynyl (propargyl), 2-butenyl, 3-butynyl, 1-hexynyl, 2-hexynyl, 3-hexynyl, 1-ethynylcyclohexyl and the like; alkoxyalkyl preferably includes those members which contain a total of from 2 to 8 carbon atoms, inclusive, for example, methoxymethyl, methoxyethyl, methoxypropyl, ethoxyethyl, propoxymethyl, propoxypropyl, methoxybutyl and the like; cycloalkyl preferably includes, unless otherwise provided for, those members which contain from 3 to 7 carbon atoms, inclusive, for example, cyclopropyl, cyclobutyl, cyclopentyl, cyclohexyl, and the like; $R_1$ and $R_2$ taken together along with the nitrogen, and $R_3$ and $R_4$ taken together along with the nitrogen, form non-aromatic heterocyclic ring, preferably includes, unless otherwise provided for, those members which contain from 2 to 6 carbon atoms, inclusive, for example, including those divalent radicals derived from normal alkanes or alkenes by removal of a hydrogen atom from each of the two terminal carbon atoms of the chain, for example, ethylene, trimethylene, tetramethylene, pentamethylene, hexamethylene, butene-2 and pentene-2; also included are those branch chain members wherein said branched member is a lower alkyl of from 1 to 4 carbon atoms, including such as ethylethylene, methylpentamethylene, 3-methylpentamethylene and the like, and with another heteroatoms, such as nitrogen or oxygen radicals such as in β-oxydiethylene and β-iminodiethylene.

The compounds of this invention have been found to be active herbicides of a general type. Included in the compounds active as herbicides and therefore useful in the method of controlling undesirable vegetation, are those compounds in which $R_1$, $R_2$, $R_3$ and $R_4$ are each methyl. That is, certain members of the class have been found to be herbicidally effective against a wide range of plant species. A method of controlling undesirable vegetation of the present invention comprises applying an herbicidally effective amount of the above-described compounds to the area or plant locus where control is desired.

An herbicide is used herein to mean a compound which controls or modifies the growth of plants. By a "growth controlling amount" is meant an amount of compound which causes a modifying effect upon the growth of plants. Such modifying effects include all deviations from natural development, for example, killing, retardation, defoliation, desiccation, regulation, stunting, tillering, stimulation, dwarfing and the like. By "plants", it is meant germinant seeds, emerging seedlings, and established vegetation, including the roots and above-ground portions.

The intermediate α-halosuccinoyl chlorides are prepared from the α-halosuccinic acid and phosphorus pentachloride according to the procedure of Freudenberg and Lux, Ber. 61B, pp. 1083–9 at p. 1087 (1928). This reference also discloses the compound bromosuccinic acid-bis-dimethyl amide. According to the procedure by Walden, Ber. 26, p. 214 (1893) hydroxy succinic acid (malic acid) can be reacted with phosphorus pentachloride to prepare the corresponding diacid chlorides.

The bis-substituted succinamides are prepared by several different methods, depending upon the nature of the starting materials and products desired. A preferred method, for example, is the reaction of a desired primary or secondary amine with the α-halosuccinoyl chloride in a suitable solvent such as benzene, methylene, chloride, diethyl ether and the like. The use of a solvent is useful to facilitate processing of the reaction and to aid in the agitation by providing adequate volume, as well as solubilizing the reagents. The preferred ratio of amine to acid chloride is 4 to 1. When the amine is used in excess as preferred, the amine acts as an acid acceptor in the reaction. Other amines, such as tertiary amines, can be employed as acid acceptors when the ratio of reactant amine to α-halosuccinoyl chloride is 2 to 1. The addition of reagents in the reaction preferably is such that permits the amine to be added to the α-halosuccinoyl chloride in solution. The temperatures for the reaction are best defined between about −30° C. and about +10° C. At these temperatures, the reaction as described hereinabove proceeds rapidly to yield the desired product. In each instance after the reaction is complete, the recovery is carried out by normal work-up procedures, such as crystallization, sublimation or distillation.

The compounds of the present invention and their preparation are more particularly illustrated by the following examples. Following the examples is a table of compounds which are prepared according to the procedures described herein.

EXAMPLE I

Preparation of Bis-N,N-diallyl-α-bromosuccinamide

A solution of 11.7 g. diallylamine (0.12 mole) in 25 ml. methylene chloride (0.03 mole) in 75 ml. methylene chloride at −30° to −25° C. The reaction mixture was stirred for ½ hour after amine addition was complete during which time the temperature rose to 10° C.

The product was stirred with 100 ml. water, phase separated and then washed with two 100 ml. portions of 5% sulfuric acid solution and one 100 ml. portion of 5% sodium bicarbonate solution. The organic solution was dried over magnesium sulfate, filtered, and the solvent evaporated under vacuum. There was obtained 8.1 g. of the title compound $N_D^{30}=1.5196$.

EXAMPLE II

Preparation of N,N'-dibenzyl-α-bromosuccinamide

A solution of 7.3 g. benzylamine (0.068 mole) and 8.2 g. N,N-dimethylaniline (0.068 mole) in 25 ml. methylene chloride was added dropwise with stirring to 8.0 g. α-bromosuccinoyl chloride (0.034 mole) in 75 ml. methylene chloride at −30° C. to −25° C. The reaction mixture was washed with 100 ml. water. The insoluble solid was removed by filtration and air-dried to give 2.9 g. of the title compound, m.p. 232° C. (dec.). Identification was confirmed by n.m.r. analysis.

EXAMPLE III

Preparation of N,N'-dipiperidino-α-chlorosuccinamide (1,1'-dichlorosuccinoyl dipiperidine)

A solution of 8.9 g. piperidine (0.104 mole) in 25 ml. methylene chloride was added dropwise with stirring to a solution of 5.0 g. (0.026 mole) α-chlorosuccinoyl chloride in 75 ml. methylene chloride at −30° to −25° C. The reaction mixture was stirred for ½ hour after addition was complete, during which time the temperature rose to 12° C.

The mixture was next stirred with 100 ml. of water, phase separated and the organic layer was washed successively with two 100 ml. portions of dilute hydrochloric acid and two 100 ml. portions of water.

After drying over magnesium sulfate, the solvent was removed in vacuum to leave an oil, 6.5 g., $N_D^{30}=1.5111$, identified by n.m.r. analysis to be the title compound.

EXAMPLE IV

Preparation of Bis-N,N-diethyl-α-bromosuccinamide

A solution of 6.9 g. diethylamine (0.09 mole) in 75 ml. toluene and 6.4 g. 50% aqueous sodium hydroxide (0.08 mole) diluted with 10 ml. water were mixed and cooled to −15° C. A solution of 10.0 g. α-bromosuccinoyl chloride (0.04 mole) in 10 ml. toluene was added dropwise to the mixture with rapid stirring at −15° to −10° C. The reaction mixture was stirred for ½ hour after addition was complete, during which time the temperature rose to 15° C.

The mixture was phase separated and the organic layer was washed successively with 100 ml. water, two 100 ml. portions of dilute hydrochloric acid and two 100 ml. portions of water.

After drying over magnesium sulfate, the solvent was removed in vacuum. There was obtained an oil, 8.9 g., $N_D^{30}=1.4955$, identified by n.m.r. analysis to be the title compound.

The following is a table of compounds which are prepared according to the aforementioned procedures. Compound numbers have been assigned to them and are used for identification throughout the balance of the specification.

TABLE I

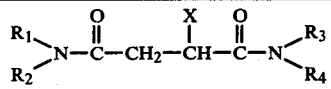

| COMPOUND NUMBER | X | R₁ | R₂ | R₃ | R₄ | m.p. °C. or $N_D^{30}$ |
|---|---|---|---|---|---|---|
| 1 | Br | H | (CH₃)₃C | H | (CH₃)₃C | 179° (dec.) |
| 2 | Br | CH₂=CHCH₂ | CH₂=CHCH₂ | CH₂=CHCH₂ | CH₂=CHCH₂ | 1.5196 |
| 3 | Br | CH₃CH₂CH | CH₂=CClCH₂ | CH₃CH₂CH₂ | CH₂=CClCH₂ | 1.5154 |
| 4 | Br | φCH₂ | H | φCH₂ | H | 232° (dec.) |
| 5 | Br | CH₂=CHCH₂ | CH₂=CClCH₂ | CH₂=CHCH₂ | CH₂=CClCH₂ | 1.5355 |
| 6 | Cl | CH₂=CHCH₂ | CH₂=CClCH₂ | CH₂=CHCH₂ | CH₂=CClCH₂ | 1.521 |
| 7 | Br | CH₃CH₂CH₂ | CH₃CH₂CH₂ | CH₃CH₂CH₂ | CH₃CH₂CH₂ | 1.4863 |
| 8 | Br | CH₃CH₂CH₂ | CH₂=CHCH₂ | CH₃CH₂CH₂ | CH₂=CHCH₂ | 1.5046 |
| 9 | Br | CH₃O(CH₂)₃— | H | CH₃O(CH₂)₃— | H | 107–110 |
| 10 | Cl | CH₂=CHCH₂ | CH₂=CHCH₂ | CH₂=CHCH₂ | CH₂=CHCH₂ | 1.5082 |
| 11 | Cl | | —(CH₂)₅— | | —(CH₂)₅— | 1.5111 |
| 12 | Br | CH₃ | CH≡CCH(CH₃) | CH₃ | CH≡CCH(CH₃) | 1.5178 |
| 13 | Br | C₂H₅ | C₂H₅ | C₂H₅ | C₂H₅ | 1.4955 |
| 14 | Cl | CH₃ | C₂H₅ | CH₃ | C₂H₅ | |

TABLE I-continued $$R_1R_2N-C(=O)-CH_2-CH(X)-C(=O)-NR_3R_4$$

| COMPOUND NUMBER | X | $R_1$ | $R_2$ | $R_3$ | $R_4$ | m.p. °C. or $N_D^{30}$ |
|---|---|---|---|---|---|---|
| 15 | Br |  | tetrahydropyran-yl |  | tetrahydropyran-yl | dark solid |
| 16 | Br | $CH_3-$ | $C_6H_5CH_2-$ | $CH_3-$ | $C_6H_5CH_2-$ | 1.5651 |
| 17 | Cl |  | $-(CH_2)_4-$ |  | $-(CH_2)_4-$ | 64–68 |
| 18 | Br | $CH_2=CHCH_2-$ | tetrahydrothiopyran-yl | $CH_2=CHCH_2-$ | tetrahydrothiopyran-yl | 1.5250 |
| 19 | Br | $CH_3-$ | tetrahydrothiopyran-yl | $CH_3-$ | tetrahydrothiopyran-yl | 1.5238 |
| 20 | Br | $CH_3CH_2-$ | $CH_2=CHCH_2-$ | $CH_3CH_2-$ | $CH_2=CHCH_2$ | 1.5095 |
| 21 | Br | $CH_3-$ | $CH_2=CHCH_2$ | $CH_3-$ | $CH_2=CHCH_2-$ | 1.5178 |
| 22 | Br |  | $-(CH_2)_5-$ |  | $-(CH_2)_5-$ | 1.5296 |
| 23 | Br | n-$C_4H_9$ | $CH_2=CHCH_2$ | n-$CH_9$ | $CH_2=CHCH_2$ | 1.4984 |
| 24 | Br | $CH_3CHCH_2-$ (branched, $CH_3$) | $CH_2=CHCH_2-$ | $CH_3CHCH_2-$ (branched, $CH_3$) | $CH_2=CHCH_2-$ | 1.4969 |
| 25 | Br | $HC\equiv CCH_2-$ | $HC\equiv CCH_2$ | $HC\equiv CCH_2-$ | $HC\equiv CCH_2-$ | 1.5323 |
| 26 | Cl | $HC\equiv CCH_2-$ | $HC\equiv CCH_2$ | $HC\equiv CCH_2-$ | $HC\equiv CCH_2-$ |  |
| 27 | Br | $CH_3-$ | tetrahydrofuran-2-yl-$CH_2-$ | $CH_3-$ | tetrahydrofuran-2-yl-$CH_2-$ | 1.5156 |
| 28 | Cl | $CH_3-$ | tetrahydrofuran-2-yl-$CH_2-$ | $CH_3-$ | tetrahydrofuran-2-yl-$CH_2-$ |  |
| 29 | Br | $BrCH_2CH_2CH_2-$ | H | $BrCH_2CH_2CH_2$ | H | 106° (dec.) |
| 30 | Cl | $BrCH_2CH_2CH_2-$ | H | $BrCH_2CH_2CH_2$ | H |  |
| 31 | Br | H | $CH\equiv CC(CH_3)_2$ | H | $CH\equiv CC(CH_3)_2$ | 123° (dec.) |
| 32 | Br |  | $-(CH_2)_6-$ |  | $-(CH_2)_6-$ | 1.5322 |
| 33 | Br | H | $CH_2CH_2CH_3$ | H | $CH_2CH_2CH_3$ | 155°–157° |
| 34 | Cl | H | $CH_2CH=CH_2$ | H | $CH_2CH=CH_2$ | 170°–171° |
| 35 | Br | H | $HC\equiv CCH_2$ | H | $HC\equiv CCH_2$ | 148°–149° |
| 36 | Br | H | $CH_3(CH_2)_4$ | H | $CH_3(CH_2)_4$ | 140°–143° |
| 37 | Br | H | tetrahydrothiopyran-yl | H | tetrahydrothiopyran-yl | 186° (dec.) |
| 38 | Cl |  | cyclohexenyl |  | cyclohexenyl | 72°–79° |
| 39 | Br |  | cyclohexenyl |  | cyclohexenyl | 79°–82° |
| 40 | Br | H | $CH_3CH-CHCH_2$ | H | $CH_3CH-CHCH_2$ | 166°–167° |
| 41 | Br | H | furan-2-yl-$CH_2$ | H | furan-2-yl-$CH_2$ | 161° (dec.) |
| 42 | Br | H | $CH_2=C(CH_3)CH_2$ | H | $CH_2=C(CH_3)CH_2$ | 145° (dec.) |
| 43 | Br | H | $(CH_3)_2CH(CH_2)_2$ | H | $(CH_3)_2CH(CH_2)_2$ | 122°–126° |
| 44 | Cl |  | 4-methylcyclohexyl |  | 4-methylcyclohexyl | 1.5098 |

TABLE I-continued $$R_1R_2N-C(=O)-CH_2-CH(X)-C(=O)-NR_3R_4$$

| COMPOUND NUMBER | X | R$_1$ | R$_2$ | R$_3$ | R$_4$ | m.p. °C. or $N_D^{30}$ |
|---|---|---|---|---|---|---|
| 45 | Cl |  | 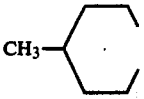 |  | 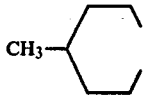 | 1.5052 |
| 46 | Br | BrCH$_2$CH$_2$ | H | BrCH$_2$CH$_2$ | H | 156° (dec.) |
| 47 | Cl |  |  |  |  | 102°–104° |
| 48 | Br | H | CH$_2$=CClCH$_2$ | H | CH$_2$=CClCH$_2$ | 166°–167° (dec.) |
| 49 | Br | H | CH$_3$ | H | CH$_3$ | 153°–155° |
| 50 | Br | H | CH$_2$CH$_3$ | H | CH$_2$CH$_3$ | 180°–181° |
| 51 | Br | H | (CH$_3$)$_2$CH | H | (CH$_3$)$_2$CH | 169° (dec.) |
| 52 | Br | H | CH$_3$(CH$_2$)$_3$ | H | CH$_3$(CH$_2$)$_3$ | 141°–142° |
| 53 | Br | H | (CH$_3$)$_2$CHCH$_2$ | H | (CH$_3$)$_2$CHCH$_2$ | 141°–142° |
| 54 | Br | H | CH$_3$CH$_2$CH(CH$_3$) | H | CH$_3$CH$_2$CH(CH$_3$) | 158°–161° |
| 55 | Br | H | (CH$_3$)$_2$CHCH$_2$CH(CH$_3$) | H | (CH$_3$)$_2$CHCH$_2$CH(CH$_3$) | 128°–131° |
| 56 | Br | H | CH$_3$(CH$_2$)$_5$ | H | CH$_3$(CH$_2$)$_5$ | 126°–127° |
| 57 | Br | H | CH$_3$(CH$_2$)$_2$CH(CH$_3$) | H | CH$_3$(CH$_2$)$_2$CH(CH$_3$) | 164°–165° |
| 58 | Br | H | (CH$_3$CH$_2$)$_2$CH | H | (CH$_3$CH$_2$)$_2$CH | 169° (dec.) |
| 59 | Br | H | ClCH=CHCH$_2$ | H | ClCH=CHCH$_2$ | 150° (dec.) |
| 60 | Br | H | Cl$_2$C=CHCH$_2$ | H | Cl$_2$C=CHCH$_2$ | 167° |
| 61 | Br | H | 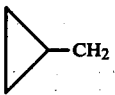 | H | 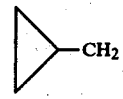 | 172° (dec.) |
| 62 | Br | H | CH$_2$=CH(CH$_2$)$_2$ | H | CH$_2$=CH(CH$_2$)$_2$ | 145°–149° |
| 63 | Br | H | CH$_2$CH=CH$_2$ | H | CH$_2$CH=CH$_2$ | 156°–159° |
| 64 | Br | H | (CH$_2$)$_3$CH=CH$_2$ | H | (CH$_2$)$_3$CH=CH$_2$ | 127°–130° |
| 65 | Br | H | CH$_2$CCl=CHCl | H | CH$_2$CCl=CHCl | 140–141.5 |
| 66 | Br | H | cycloheptyl | H | cycloheptyl | 174° (dec.) |
| 67 | Cl | CH$_3$CH$_2$CH$_2$ | CH$_2$CCl=CH$_2$ | CH$_3$CH$_2$CH$_2$ | CH$_2$CCl=CH$_2$ | 1.5069 |
| 68 | Br | H | cyclopentyl | H | cyclopentyl | 170° (dec.) |
| 69 | Cl | H | CH$_2$CCl=CH$_2$ | H | CH$_2$CCl=CH$_2$ | 164° (dec.) |
| 70 | Cl | H | CH$_2$C≡CH | H | CH$_2$C≡CH | 145° (dec.) |
| 71 | Br | H | CH$_3$CH$_2$CH(CH$_3$)CH(CH$_3$) | H | CH$_3$CH$_2$CH(CH$_3$)CH(CH$_3$) | 135°–137° |
| 72 | Br | H | CH$_3$(CH$_2$)$_3$CH(CH$_3$) | H | CH$_3$(CH$_2$)$_3$CH(CH$_3$) | 120°–124° |
| 73 | Br | H | CH$_3$(CH$_2$)$_2$CH(CH$_3$)CH$_2$ | H | CH$_3$(CH$_2$)$_2$CH(CH$_3$)CH$_2$ | 111–114 |
| 74 | Br | H | 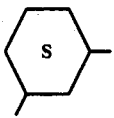 | H |  | 160° (dec.) |
| 75 | Br | H |  | H |  | 66° (dec.) |
| 76 | Cl | H | CH$_3$CH$_2$CH(CH$_3$) | H | CH$_3$CH$_2$CH(CH$_3$) | 170° (dec.) |
| 77 | Br | H | (CH$_3$)$_2$C=CHCH$_2$ | H | (CH$_3$)$_2$C=CHCH$_2$ | 157° (dec.) |
| 78 | Br | H | CH$_3$CH=CHCH(CH$_3$) | H | CH$_3$CH=CHCH(CH$_3$) | 138°–143° |
| 79 | Cl | H |  | H |  | 178°–180° |
| 80 | Cl | H | CH$_3$CH=CHCH$_2$ | H | CH$_3$CH=CHCH$_2$ | 164°–166° |
| 81 | Br | H | CH$_3$CCl=CHCH$_2$ | H | CH$_3$CCl=CHCH$_2$ | 166°–169° |
| 82 | Cl | H | CH$_2$=C(CH$_3$)CH$_2$ | H | CH$_2$=C(CH$_3$)CH$_2$ | 165° (dec.) |
| 83 | Cl | CH$_3$CH$_2$CH$_2$ | CH$_2$=CHCH$_2$ | CH$_3$CH$_2$CH$_2$ | CH$_2$=CHCH$_2$ | 1.4926 |
| 84 | Cl | CH$_3$CH$_2$CH$_2$ | CH$_3$CH$_2$CH$_2$ | CH$_3$CH$_2$CH$_2$ | CH$_3$CH$_2$CH$_2$ | 1.4789 |
| 85 | Cl | CH$_2$=CHCH$_2$ | CH$_2$=CClCH$_2$ | CH$_2$=CHCH$_2$ | CH$_2$=CClCH$_2$ | 1.5210 |
| 86 | Cl | H | CH$_3$ | H | CH$_3$ | 141°–143° |
| 87 | Cl | H | C$_2$H$_5$ | H | C$_2$H$_5$ | 195°–197° |
| 88 | Cl | H | CH$_3$CH$_2$CH$_2$ | H | CH$_3$CH$_2$CH$_2$ | 173°–176° |
| 89 | Cl | H | (CH$_3$)$_2$CH | H | (CH$_3$)$_2$CH | 190° (dec.) |
| 90 | Cl | H | CH$_3$(CH$_2$)$_3$ | H | CH$_3$(CH$_2$)$_3$ | 142°–144° |
| 91 | Cl | H | (CH$_3$)$_2$CHCH$_2$ | H | (CH$_3$)$_2$CHCH$_2$ | 165° (dec.) |
| 92 | Cl | H | CH$_3$(CH$_2$)$_4$ | H | CH$_3$(CH$_2$)$_4$ | 125°–129° |
| 93 | Cl | H | (CH$_3$)$_2$CH(CH$_2$)$_2$ | H | (CH$_3$)$_2$CH(CH$_2$)$_2$ | 119°–124° |

TABLE I-continued

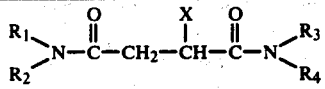

| COMPOUND NUMBER | X | R$_1$ | R$_2$ | R$_3$ | R$_4$ | m.p. °C. or N$_D^{30}$ |
|---|---|---|---|---|---|---|
| 94 | Cl | H | CH$_3$(CH$_2$)$_2$CH(CH$_3$) | H | CH$_3$(CH$_2$)$_2$CH(CH$_3$) | 160° (dec.) |
| 95 | Cl | H | CH$_3$CH$_2$CH(CH$_3$)CH(CH$_3$) | H | CH$_3$CH$_2$CH(CH$_3$)CH(CH$_3$) | 120°–125° |
| 96 | Cl | H | CH$_3$(CH$_2$)$_3$CH(CH$_3$) | H | CH$_3$(CH$_2$)$_3$CH(CH$_3$) | 108°–111° |

HERBICIDAL SCREENING TESTS

As previously mentioned, the herein described compounds produced in the above-described manner are phytotoxic compounds which are useful and valuable in controlling various plant species. Compounds of this invention are tested as herbicides in the following manner.

Pre-emergence Herbicide Screening Test

Using an analytical balance, 20 mg. of the compound to be tested is weighed out on a piece of glassine weighing paper. The paper and compound are placed in a 30 ml. wide-mouth bottle and 3 ml. of acetone containing 1% Tween 20 ® (polyoxyethylene sorbitan monolaurate) is added to dissolve the compound. If the material is not soluble in acetone, another solvent such as water, alcohol or dimethylformamide (DMF) is used instead. When DMF is used, only 0.5 ml. or less is used to dissolve the compound and then another solvent is used to make the volume up to 3 ml. The 3 ml. of solution is sprayed uniformly on the soil contained in a small flat one day after planting weed seeds in the flat of soil. An atomizer is used to apply the spray using compressed air at a pressure of 5 lb./sq. inch. The rate of application is 8 lb/acre and the spray volume is 143 gallons per acre.

On the day preceeding treatment, the flat which is 7 inches long, 5 inches wide and 2.75 inches deep, is filled to a depth of 2 inches with loamy sand soil. Seeds of seven different weed species are planted in individual rows using one species per row across the width of the flat. The seeds are covered with soil so that they are planted at a depth of 0.5 inch. Ample seeds are planted to give about 20 to 50 seedlings per row after emergence depending on the size of the plants.

The seeds used are foxtail (*Setaria spp.*)—FT; watergrass (*Echinochloa crusgalli*)—WG; red oat (*Avena sativa*)—RO; redroot pigweed (*Amaranthus retroflexus-*)—PW; mustard (*Brassica juncea*)—MD; curly dock (*Rumex crispus*)—CD; and hairy crabgrass (*Digitaria sanguinalis*)—CG.

After treatment, the flats are placed in the greenhouse at a temperature of 70° to 85° F. and watered by sprinkling. Two weeks after treatment, the degree of injury or control is determined by comparison with untreated check plants of the same age. The injury rating from 0 to 100% is recorded for each species as percent control with 0% representing no injury and 100% representing complete kill.

Post-emergence Herbicide Screening Test

Seeds of six plant species, including hairy crabgrass (CG), watergrass (WG), red oat (RO), mustard (MD), curly dock (CD) and Pinto beans (*Phaseolus vulgaris*) (BN), are planted in the flats as described above for pre-emergence screening. The flats are planted in the greenhouse at 70° to 85° F. and watered daily with a sprinkler. About 10 to 14 days after planting when the primary leaves of the bean plants are almost fully expanded and the first trifoliate leaves are just starting to form, the plants are sprayed. The spray is prepared by weighing out 20 mg. of the test compound, dissolving it in 5 ml. of acetone containing 1% Tween 20 ® (polyoxyethylene sorbitan monolaurate) and then adding 5 ml. of water. The solution is sprayed on the foliage using an atomizer at an air pressure of 5 lb/sq. inch. The spray concentration is 0.2% and the rate is 8 lb/acre. The spray volume is 476 gallons per acre.

The results of these tests are shown in Table II.

TABLE II
HERBICIDAL ACTIVITY - SCREENING RESULTS
Per Cent Control at 8 lb/A.

| COMPOUND NUMBER | CG | FT | WG | RO | PW | MD | CD |
|---|---|---|---|---|---|---|---|
| 1 | 90 | 95 | 100 | 30 | 0 | 0 | 0 |
| 2 | 100 | 100 | 100 | 100 | 100 | 100 | 50 |
| 3 | 100 | 99 | 100 | 99 | 98 | 80 | 40 |
| 4 | 80 | 50 | 50 | 40 | 0 | 20 | 20 |
| 5 | 100 | 100 | 100 | 99 | 98 | 100 | 30 |
| 6 | 100 | 99 | 99 | 98 | 100 | 80 | 20 |
| 7 | 100 | 99 | 100 | 98 | 90 | 90 | 20 |
| 8 | 99 | 100 | 99 | 100 | 99 | 90 | 80 |
| 9 | 90 | 90 | 90 | 80 | 20 | 10 | 10 |
| 10 | 100 | 98 | 99 | 98 | 50 | 80 | 30 |
| 11 | 100 | 99 | 99 | 95 | 100 | 60 | 20 |
| 12 | 100 | 100 | 100 | 98 | 100 | 80 | 30 |
| 15 | 90 | 80 | 70 | 0 | 0 | 0 | 0 |
| 16 | 80 | 80 | 70 | 40 | 0 | 0 | 0 |
| 17 | 90 | 90 | 80 | 0 | 0 | 0 | 10 |
| 18 | 20 | 0 | 0 | 0 | 0 | 0 | 0 |
| 19 | 95 | 80 | 90 | 70 | 0 | 0 | 0 |
| 20 | 98 | 98 | 100 | 95 | 80 | 40 | 20 |
| 21 | 90 | 90 | 80 | 70 | 0 | 0 | 0 |
| 23 | 100 | 100 | 100 | 95 | 80 | 20 | 30 |
| 24 | 98 | 100 | 98 | 90 | 80 | 20 | 20 |
| 25 | 100 | 100 | 95 | 90 | 70 | 10 | 10 |
| 31 | 80 | 70 | 70 | 10 | 0 | 0 | 0 |
| 32 | 100 | 90 | 90 | 70 | 0 | 0 | 10 |
| 33 | 100 | 100 | 100 | 90 | 70 | 80 | 20 |
| 34 | 90 | 100 | 95 | 70 | 0 | 0 | 0 |
| 35 | 100 | 100 | 100 | 80 | 100 | 100 | 70 |
| 36 | 100 | 100 | 100 | 80 | 20 | 40 | 0 |
| 37 | 100 | 100 | 100 | 60 | 0 | 0 | 0 |
| 38 | 100 | 100 | 100 | 98 | 100 | 98 | 90 |
| 39 | 100 | 99 | 100 | 100 | 50 | 50 | 50 |
| 40 | 98 | 98 | 100 | 95 | 30 | 40 | 30 |
| 41 | 100 | 100 | 100 | 95 | 70 | 20 | 20 |
| 42 | 100 | 100 | 100 | 95 | 0 | 40 | 30 |
| 43 | 99 | 98 | 100 | 90 | 20 | 50 | 20 |
| 44 | 100 | 100 | 100 | 40 | 70 | 60 | 20 |
| 45 | 100 | 100 | 100 | 20 | 80 | 60 | 0 |
| 47 | 100 | 98 | 100 | 60 | 0 | 10 | 0 |
| 48 | 100 | 100 | 100 | 70 | 0 | 0 | 0 |
| 49 | 80 | 80 | 80 | 60 | 0 | 0 | 0 |
| 50 | 98 | 98 | 100 | 98 | 0 | 20 | 0 |
| 51 | 98 | 98 | 100 | 100 | 0 | 20 | 10 |
| 52 | 98 | 100 | 100 | 80 | 0 | 40 | 0 |
| 53 | 98 | 100 | 100 | 90 | 0 | 50 | 0 |
| 54 | 98 | 100 | 100 | 100 | 80 | 50 | 20 |

TABLE II-continued

| | | | | | | | |
|---|---|---|---|---|---|---|---|
| 55 | 100 | 100 | 100 | 20 | 0 | 0 | 0 |
| 56 | 90 | 98 | 100 | 20 | 0 | 0 | 0 |
| 57 | 100 | 100 | 100 | 98 | 0 | 90 | 50 |
| 58 | 100 | 100 | 100 | 100 | 0 | 0 | 0 |
| 59 | 100 | 100 | 100 | 80 | 0 | 0 | 0 |
| 60 | 80 | 90 | 90 | 0 | 0 | 0 | 0 |
| 61 | 95 | 100 | 100 | 90 | 20 | 20 | 10 |
| 62 | 100 | 100 | 100 | 80 | 0 | 20 | 0 |
| 63 | 99 | 100 | 100 | 98 | 60 | 60 | 30 |
| 64 | 100 | 100 | 100 | 70 | 0 | 0 | 0 |
| 65 | 100 | 80 | 80 | 0 | 0 | 0 | 0 |
| 66 | 70 | 80 | 70 | 0 | 0 | 0 | 0 |
| 67 | 100 | 100 | 80 | 0 | 0 | 0 | 0 |
| 68 | 100 | 100 | 100 | 80 | 0 | 0 | 0 |
| 69 | 80 | 80 | 80 | 10 | 0 | 0 | 0 |
| 70 | 70 | 70 | 70 | 10 | 0 | 0 | 0 |
| 71 | 90 | 80 | 80 | 20 | 0 | 0 | 0 |
| 72 | 90 | 90 | 95 | 40 | 10 | 0 | 0 |
| 73 | 90 | 98 | 95 | 0 | 0 | 0 | 0 |
| 74 | 98 | 100 | 100 | 70 | 20 | 10 | 10 |
| 75 | 90 | 90 | 80 | 20 | 0 | 0 | 0 |
| 76 | 90 | 90 | 80 | 80 | 0 | 0 | 0 |
| 77 | 90 | 90 | 90 | 20 | 0 | 0 | 0 |
| 78 | 100 | 100 | 100 | 98 | 50 | 40 | 30 |
| 79 | 30 | 30 | 10 | 10 | 0 | 0 | 0 |
| 80 | 80 | 80 | 80 | 0 | 0 | 0 | 0 |
| 81 | 90 | 95 | 95 | 0 | 0 | 0 | 0 |
| 82 | 95 | 95 | 95 | 10 | 0 | 0 | 0 |
| 83 | 100 | 100 | 100 | 90 | 0 | 0 | 0 |
| 84 | 98 | 95 | 98 | 60 | 0 | 0 | 0 |
| 85 | 100 | 100 | 100 | 60 | 0 | 0 | 0 |
| 86 | 0 | 0 | 0 | 0 | 0 | 0 | 0 |
| 87 | 0 | 0 | 0 | 0 | 0 | 0 | 0 |
| 88 | 95 | 98 | 98 | 0 | 0 | 0 | 0 |
| 89 | 98 | 98 | 98 | 30 | 50 | 0 | 0 |
| 90 | 98 | 98 | 98 | 50 | 0 | 0 | 0 |
| 91 | 98 | 95 | 95 | 50 | 0 | 0 | 0 |
| 92 | 90 | 80 | 95 | 10 | 0 | 0 | 0 |
| 93 | 90 | 20 | 30 | 0 | 0 | 0 | 0 |
| 94 | 99 | 98 | 95 | 0 | 0 | 0 | 0 |
| 95 | 90 | 70 | 10 | 0 | 0 | 0 | 0 |
| 96 | 99 | 98 | 98 | 10 | 0 | 0 | 0 |

| COMPOUND NUMBER | Post-emergence | | | | | |
|---|---|---|---|---|---|---|
| | CG | WG | RO | MD | CD | BN |
| 1 | 0 | 0 | 0 | 0 | 0 | 0 |
| 2 | 90 | 95 | 70 | 100 | 0 | 98 |
| 3 | 80 | 80 | 80 | 90 | 0 | 60 |
| 4 | 20 | 0 | 0 | 10 | 0 | 20 |
| 5 | 90 | 80 | 80 | 90 | 0 | 0 |
| 6 | 80 | 70 | 70 | 100 | 0 | 70 |
| 7 | 50 | 50 | 40 | 20 | 10 | 20 |
| 8 | 80 | 80 | 60 | 90 | 20 | 80 |
| 9 | 90 | 70 | 30 | 30 | 0 | 20 |
| 10 | 80 | 70 | 50 | 100 | 100 | 80 |
| 11 | 50 | 40 | 60 | 80 | 0 | 80 |
| 12 | 90 | 80 | 70 | 100 | 20 | 100 |
| 15 | 70 | 20 | 10 | 0 | 0 | 0 |
| 16 | 70 | 60 | 40 | 10 | 10 | 10 |
| 17 | 80 | 60 | 20 | 30 | 10 | 30 |
| 18 | 40 | 50 | 10 | 20 | 0 | 0 |
| 19 | 80 | 70 | 0 | 0 | 0 | 20 |
| 20 | 90 | 80 | 70 | 90 | 20 | 100 |
| 21 | 80 | 70 | 60 | 0 | 0 | 0 |
| 23 | 100 | 100 | 70 | 90 | 30 | 10 |
| 24 | 95 | 90 | 80 | 100 | 10 | 10 |
| 25 | 90 | 90 | 80 | 20 | 10 | 30 |
| 27 | 80 | 20 | 10 | 0 | 0 | 0 |
| 31 | 70 | 50 | 10 | 10 | 10 | 20 |
| 32 | 80 | 80 | 70 | 0 | 0 | 0 |
| 33 | 80 | 90 | 70 | 80 | 20 | 100 |
| 34 | 80 | 80 | 80 | 30 | 10 | 80 |
| 35 | 80 | 80 | 80 | 20 | 20 | 100 |
| 36 | 80 | 80 | 70 | 80 | 10 | 100 |
| 37 | 80 | 100 | 70 | 0 | 0 | 80 |
| 38 | 90 | 90 | 50 | 80 | 20 | 80 |
| 39 | 80 | 80 | 60 | 10 | 0 | 10 |
| 40 | 80 | 100 | 60 | 70 | 20 | 100 |
| 41 | 80 | 90 | 70 | 20 | 0 | 80 |
| 42 | 90 | 90 | 60 | 20 | 20 | 80 |
| 43 | 80 | 80 | 60 | 20 | 20 | 70 |
| 44 | 100 | 100 | 60 | 100 | 70 | 30 |
| 45 | 100 | 100 | 20 | 100 | 10 | 40 |
| 46 | 20 | 10 | 0 | 0 | 0 | 10 |
| 47 | 80 | 60 | 20 | 10 | 0 | 0 |
| 48 | 100 | 100 | 60 | 50 | 20 | 80 |
| 50 | 80 | 70 | 50 | 20 | 10 | 80 |
| 51 | 80 | 70 | 50 | 0 | 0 | 80 |
| 52 | 80 | 70 | 70 | 80 | 0 | 70 |
| 53 | 80 | 70 | 70 | 70 | 0 | 80 |
| 54 | 80 | 80 | 70 | 90 | 20 | 100 |
| 55 | 70 | 60 | 50 | 0 | 0 | 80 |
| 56 | 70 | 70 | 40 | 70 | 0 | 20 |
| 57 | 80 | 70 | 70 | 60 | 20 | 80 |
| 58 | 50 | 40 | 20 | 0 | 0 | 60 |
| 59 | 70 | 60 | 50 | 0 | 0 | 80 |
| 60 | 60 | 20 | 0 | 0 | 0 | 0 |
| 61 | 100 | 80 | 60 | 80 | 20 | 80 |
| 62 | 90 | 80 | 60 | 0 | 0 | 80 |
| 63 | 80 | 80 | 60 | 100 | 50 | 100 |
| 64 | 40 | 50 | 0 | 80 | 0 | 50 |
| 65 | 80 | 50 | 0 | 70 | 0 | 0 |
| 66 | 0 | 0 | 0 | 0 | 0 | 0 |
| 67 | 100 | 50 | 0 | 80 | 0 | 0 |
| 68 | 80 | 60 | 40 | 100 | 80 | 80 |
| 69 | 50 | 40 | 0 | 20 | 0 | 10 |
| 70 | 30 | 50 | 10 | 20 | 0 | 20 |
| 71 | 80 | 80 | 40 | 10 | 0 | 80 |
| 72 | 80 | 95 | 70 | 20 | 0 | 80 |
| 73 | 70 | 70 | 20 | 20 | 0 | 80 |
| 74 | 80 | 95 | 60 | 20 | 0 | 80 |
| 75 | 70 | 70 | 0 | 20 | 10 | 20 |
| 76 | 60 | 60 | 10 | 20 | 0 | 80 |
| 77 | 70 | 70 | 10 | 0 | 0 | 10 |
| 78 | 90 | 80 | 70 | 40 | 30 | 90 |
| 79 | 0 | 0 | 0 | 0 | 0 | 30 |
| 80 | 40 | 0 | 0 | 30 | 0 | 20 |
| 81 | 70 | 40 | 0 | 20 | 0 | 20 |
| 82 | 80 | 70 | 0 | 0 | 0 | 10 |
| 83 | 90 | 90 | 40 | 20 | 0 | 95 |
| 84 | 95 | 90 | 0 | 0 | 0 | 50 |
| 85 | 90 | 90 | 0 | 80 | 0 | 50 |
| 86 | 10 | 0 | 0 | 0 | 0 | 0 |
| 87 | 10 | 10 | 0 | 0 | 0 | 0 |
| 88 | 80 | 80 | 20 | 0 | 0 | 20 |
| 89 | 40 | 60 | 0 | 0 | 0 | 20 |
| 90 | 95 | 60 | 0 | 0 | 0 | 0 |
| 91 | 80 | 60 | 0 | 0 | 0 | 20 |
| 92 | 40 | 0 | 0 | 0 | 0 | 0 |
| 93 | 10 | 60 | 0 | 10 | 10 | 10 |
| 94 | 70 | 70 | 10 | 10 | 0 | 80 |
| 95 | 0 | 0 | 0 | 0 | 0 | 0 |
| 96 | 80 | 60 | 0 | 60 | 0 | 10 |

The compounds of the present invention are used as pre-emergence or post-emergence herbicides and are applied in a variety of ways at various concentrations. In practice, the compounds are formulated with an inert carrier, utilizing methods well-known to those skilled in the art, thereby making them suitable for application as dusts, sprays, or drenches and the like, in the form and manner required. The mixtures can be dispersed in water with the aid of a wetting agent or they can be employed in organic liquid compositions, oil and water, water in oil emulsions, with or without the addition of wetting, dispersing or emulsifying agents. An herbicidally effective amount depends upon the nature of the seeds or plants to be controlled and the rate of application varies from 0.10 to approximately 50 pounds per acre. The concentration of a compound of the present invention, constituting an effective amount in the best mode of administration in the utility disclosed, is readily determinable by those skilled in the art.

The phytotoxic compositions of this invention employing an herbicidally effective amount of the compound described herein are applied to the plants in the conventional manner. Thus, the dust and liquid compositions can be applied to the plant by the use of power dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles and these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers, pesticides and the like, used as adjuvant or in combination with any of the above-described adjuvants. Other phytotoxic compounds useful in combination with the above-described compounds include, for example, 2,4-dichlorophenoxyacetic acids, 2,4,5-trichlorophenoxyacetic acid, 2-methyl-4-chlorophenoxyacetic acid and the salts, esters and amides thereof; triazine derivatives, such as 2,4-bis(3-methoxypropylamino)-6-methyl-thio-s-triazine; 2-chloro-4-ethylamino-6-isopropylamino-s-triazine, and 2-ethylamino-4-isopropylamino-6-methyl-mercapto-s-triazine, urea derivatives, such as 3-(3,4-dichlorophenyl)-1,1-dimethyl urea and acetamides such as N,N-diallyl-α-chloroacetamide, N-(α-chloroacetyl)-hexamethyleneimine, and N,N-diethyl-α-bromoacetamide, and the like; benzoic acids such as 3-amino-2,5-dichlorobenzoic; and thiocarbamates, such as S-propyl dipropylthiocarbamate; S-ethyldipropylthiocarbamate; S-ethyl hexahydro-1H-azepine-1-carbothioate and the like. Fertilizers useful in combination with the active ingredients include, for example, ammonium nitrate, urea and superphosphate. Other useful additaments include materials in which plant organisms take root and grow, such as compost, manure, humus, sand and the like.

Various changes and modifications are possible without departing from the spirit and scope of the invention described herein and will be apparent to those skilled in the art to which it pertains. It is accordingly intended that the present invention shall only be limited by the scope of the claims.

What is claim is:

1. A method for controlling the growth of undesirable vegetation which comprises applying to the area where control of said vegetative growth is desired, an herbicidally effective amount of a compound having the formula

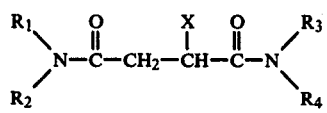

in which X is chlorine or bromine; $R_1$ and $R_2$ taken together along with the nitrogen form a non-aromatic heterocyclic ring having from 2 to 8 carbon atoms, inclusive; $R_3$ and $R_4$ taken together along with the nitrogen form a non-aromatic heterocyclic ring having from 2 to 8 carbon atoms, inclusive.

2. A method according to claim 1 in which X is bromine, $R_1$ and $R_2$ taken together and $R_3$ and $R_4$ taken together are each alkylene.

3. A method according to claim 2 in which $R_1$ and $R_2$ taken together and $R_3$ and $R_4$ taken together are each pentamethylene.

4. A method according to claim 2 in which $R_1$ and $R_2$ taken together and $R_3$ and $R_4$ taken together are each hexamethylene.

5. A method according to claim 1 in which X is chlorine, $R_1$ and $R_2$ taken together and $R_3$ and $R_4$ taken together are each alkylene.

6. A method according to claim 5 in which $R_1$ and $R_2$ taken together and $R_3$ and $R_4$ taken together are each pentamethylene.

7. A method according to claim 5 in which $R_1$ and $R_2$ taken together and $R_3$ and $R_4$ taken together are each tetramethylene.

8. A method according to claim 1 in which X is chlorine, $R_1$ and $R_2$ taken together and $R_3$ and $R_4$ taken together are each 2-methylpentamethylene.

9. A method according to claim 1 in which X is chlorine, $R_1$ and $R_2$ taken together and $R_3$ and $R_4$ taken together are each 3-methylpentamethylene.

* * * * *